United States Patent [19]

Distler et al.

[11] 4,402,085
[45] Aug. 30, 1983

[54] TOMOGRAPHIC X-RAY APPARATUS FOR THE PRODUCTION OF TRANSVERSE LAYER IMAGES

[75] Inventors: Walter Distler, Erlangen-Dechsendorf; Karl-Georg Heinzelmann, Neunkirchen, both of Fed. Rep. of Germany

[73] Assignee: Siemens Aktiengesellschaft, Berlin & Munich, Fed. Rep. of Germany

[21] Appl. No.: 238,224

[22] Filed: Feb. 26, 1981

[30] Foreign Application Priority Data

Mar. 20, 1980 [DE] Fed. Rep. of Germany ....... 3010819

[51] Int. Cl.³ .......................................... G03B 41/16
[52] U.S. Cl. ....................................... 378/15; 378/196
[58] Field of Search .......................................... 378/15

[56] References Cited

U.S. PATENT DOCUMENTS 4,063,792 12/1977 Lodge ............................... 378/15
4,190,772 2/1980 Dinwiddie et al. .
4,201,430 5/1980 Dinwiddie ....................... 378/15

Primary Examiner—Craig E. Church
Attorney, Agent, or Firm—Hill, Van Santen, Steadman & Simpson

[57] ABSTRACT

In an exemplary embodiment, the current supply of the x-ray tube proceeds via a slip ring arrangement with sliding contacts arranged between the rotating frame and the stationary apparatus part. The slip ring arrangement with the sliding contacts is provided between two coaxial rings of which one is connected with the rotating frame, and the other is stationary. The rings have axially projecting intermeshing ribs, and the central openings of the rings are designed for the purpose of insertion of the patient support.

3 Claims, 1 Drawing Figure

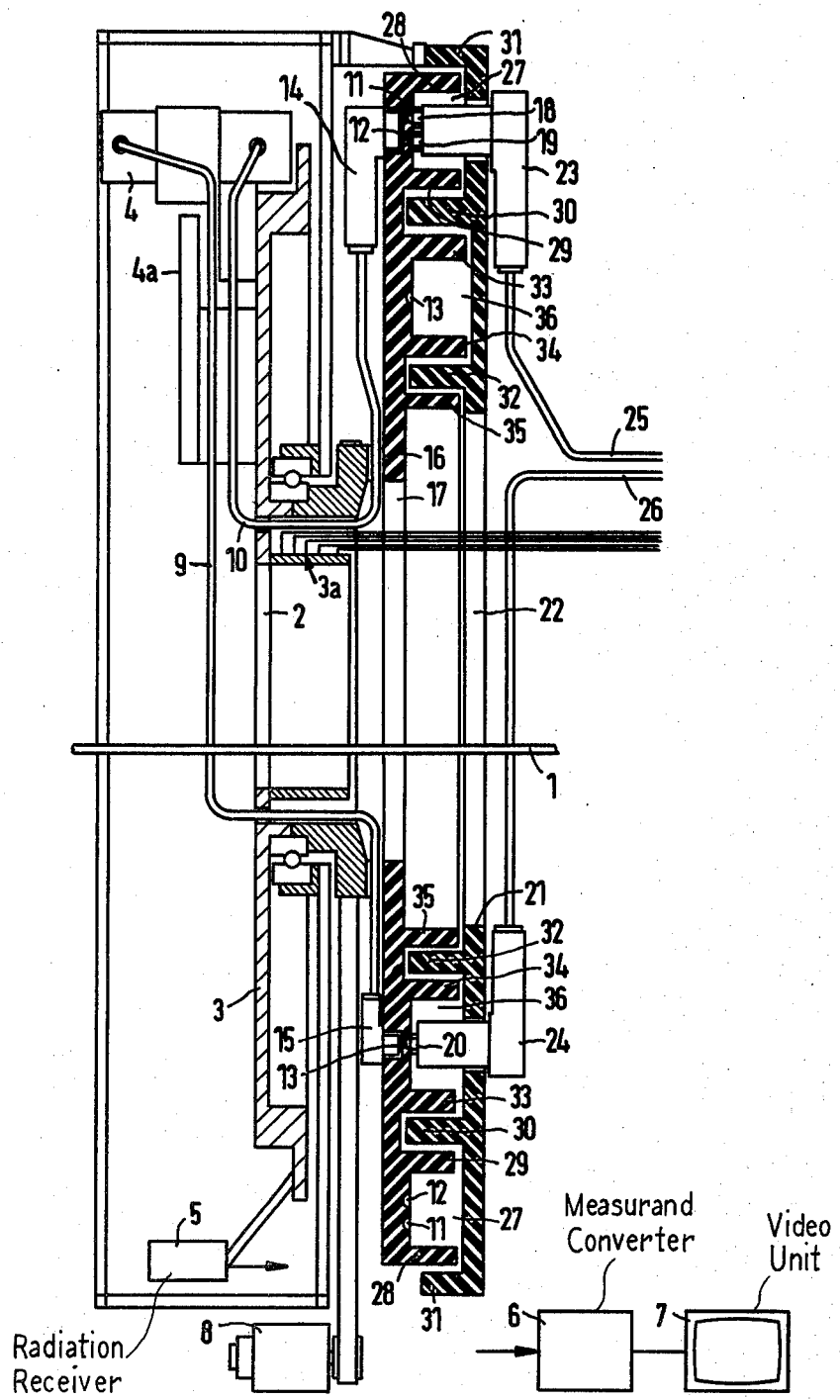

TOMOGRAPHIC X-RAY APPARATUS FOR THE PRODUCTION OF TRANSVERSE LAYER IMAGES

BACKGROUND OF THE INVENTION

The invention relates to a tomographic x-ray apparatus for the production of transverse layer images of a radiography subject, comprising a patient support, an x-ray measuring arrangement with an x-ray source supplied by an x-ray generator, which x-ray source generates an x-ray beam penetrating the radiography subject, and with a radiation receiver which determines the radiation intensity behind the subject, a drive device for the measuring arrangement with a rotating frame for generating rotational movements of the measuring arrangement, and a measurand converter for the transformation of the signals delivered by the radiation receiver into a layer image, wherein the current supply for the x-ray tube proceeds via a slip ring arrangement with sliding contacts which is arranged between the rotating frame and the stationary apparatus part.

A tomographic x-ray apparatus of this type is described, for example, in the German OS No. 27 16 818. It is designated as a computer tomograph and permits, due to the utilization of the slip rings, a permanent rotation of the measuring arrangement, and hence a very rapid scanning of the radiography subject from different directions. From the output signals of the radiation receiver formed at different projections, the measurand converter computes the attenuation coefficients of predetermined points of the examined transverse layer. The computed attenuation coefficient can be displayed in the form of a layer image on a television display unit.

In the case of the known computer tomograph, there are positioned on one shaft, several support members for the slip rings against which the sliding contacts are engaged in the radial direction. The slip rings and the sliding contacts are arranged in a receptacle filled with insulating oil. The utilization of insulating oil, however, signifies a relatively great outlay, in particular, also because this oil must be changed from time to time. In addition, in the case of the known computer tomograph, the possibility of movement of the radiography subject in the longitudinal direction of the support is restricted, since the slip ring arrangement with the sliding contact is provided at the one end of the computer tomograph and restricts the insertion path at that location.

SUMMARY OF THE INVENTION

The object underlying the invention resides in designing a tomographic x-ray apparatus of the type initially cited such that the utilization of insulating oil can be dispensed with, on the one hand, and that a free insertion of the radiography subject through the computer tomograph is possible, on the other hand.

In accordance with the invention, this object is achieved in that the slip ring arrangement with the sliding contact is provided between two coaxial rings, the one of which is connected with the rotating frame, and the other of which is stationary; the coaxial rings interengage with axially projecting ribs and whose central openings are designed for the purpose of accommodating insertion of the patient support. Due to the elongation of the leakage paths with the aid of the ribs on the rings supporting the contact arrangement, in the case of the inventive computer tomograph, air suffices as the insulating medium for the contact arrangement. Due to the fact that the members supporting the contact arrangement are designed in the form of coaxial rings, it is possible to axially insert the radiography subject through these rings such that the radiography subject can be freely located in the longitudinal direction.

It is particularly expedient to provide a total of three slip rings for the purpose of supplying the high voltage and the filament voltage to the x-ray tube, of which the two slip rings with the associated sliding contacts leading to the cathode are disposed in one chamber, and the slip ring with the associated sliding contact, leading to the anode, is disposed in a second chamber, whereby a plurality of interpenetrating ribs of the coaxial rings are disposed between the chambers. In this embodiment, the two slip rings with the respective sliding contacts, which are disposed in one chamber, serve the purpose of supplying the cathode potential and the filament voltage, and the other slip ring with the associated sliding contact serves the purpose of supplying the anode potential.

The invention shall be explained in greater detail in the following on the basis of an exemplary embodiment illustrated on the accompanying drawing sheet; and other objects, features and advantages will be apparent from this detailed disclosure and from the appended claims.

BRIEF DESCRIPTION OF THE DRAWING

The single FIGURE shows a tomographic apparatus according to the present invention, a portion of the apparatus being illustrated in longitudinal section, and associated electronic components being indicated diagrammatically.

DETAILED DESCRIPTION

In the drawing, a tomographic x-ray apparatus for the production of transverse layer images of a radiography subject is illustrated including a patient support 1 which is disposed in the central opening 2 of a rotating frame 3. Mounted on the rotating frame 3 are an x-ray tube 4 and a radiation receiver 5. The x-ray tube 4 emits a fan-shaped x-ray beam defined by means of a diaphragm 4a, which x-ray beam has marginal rays tangent to a subject circle and strikes a detector array which forms the radiation receiver 5 and is comprised of a series of individual detectors, for example, 512 individual detectors. If the radiography subject lying on the support 1 is scanned from various projections by the x-ray beam, then it is possible by means of a measurand converter 6 which contains a computer to calculate, from the output signals of the radiation receiver 5, an image of the examined transverse layer of the radiography subject in the form of a matrix of attenuation coefficients and to display the image on a video unit 7. The rotating frame 3 is driven by a drive motor 8 for the purpose of altering the irradiation direction.

The current supply for the x-ray tube 4 proceeds via high voltage cables 9 and 10 which are guided to three slip rings 11, 12, and 13, via plug-type connectors 14 and 15. The slip rings 11, 12, and 13, are disposed concentrically relative to one another on a ring 16 of insulating material which has a central opening 17 for accommodating the radiography subject and the patient support 1 and which is fixedly connected with the rotating frame 3. The stationary sliding contacts 18, 19, and 20, associated with the slip rings 11, 12 and 13, are arranged on a stationary ring 21 of insulating material, which likewise possesses a central opening 22 for the patient support 1 and the radiography subject. The sliding contacts 18, 19, 20 are mounted in a springy fashion in connectors 23 and 24. From the connectors 23 and 24 high voltage cables 25 and 26 lead to the high voltage and filament voltage generator for the x-ray tube 4.

The slip rings 11 and 12 are disposed in a chamber 27 which is bounded by two ribs 28 and 29 of the rotary ring 16. The stationary ring 22 possesses ribs 30 and 31 as well as an additional rib 32. In addition, also the rotary ring 16 possesses additional ribs 33, 34, and 35. The ribs of the ring 16 and 21 interpenetrate or intermesh in labyrinth fashion, whereby the ribs 29 and 33, as well as 34 and 35 of the ring 16 form grooves for the ribs 30 and 32 of the ring 21. As a consequence, leakage paths of such a length result that an air insulation of the slip rings 11 through 13 with the respective sliding contacts 18 through 20 is sufficient.

Thus, by way of summary, as the significant feature of the exemplary embodiment, it must be remembered that the rings 16 and 21, with axially projecting ribs and matching grooves, interpenetrate or intermesh and that their central openings are designed for the purpose of insertion of the patient support 1.

In the exemplary embodiment, a total of three slip rings, 11, 12, and 13, are provided, of which the slip rings 11 and 12, together with the associated sliding contacts 18 and 19, are disposed in a chamber 27 bounded by the ribs 28 and 29 and lead to the cathode of the x-ray tube 4 and supply the latter with the cathode potential as well as the filament voltage. The slip ring 13 serves the purpose of supplying the anode potential to the x-ray tube 4 and is disposed, together with the sliding contact 20 associated with it, in a chamber 36 which is bounded by the ribs 33 and 34. Between the chambers 27, 36, respectively interpenetrating or intermeshing ribs are disposed, so that leakage currents, in the case of utilization of air as the insulating substance, are virtually precluded.

The signal transmission from the radiation receiver 5 to the measurand converter 6 can likewise proceed via a slip ring arrangement. However, no insulation problems arise here, since only low voltages are to be transmitted. This slip ring arrangement 3a is only schematically illustrated.

It will be apparent that many modifications and variations may be effected without departing from the scope of the novel concepts and teachings of the present invention.

We claim as our invention:

1. A tomographic x-ray apparatus for the production of transverse layer images of a radiography subject, comprising a patient support, an x-ray measuring arrangement including an x-ray source, which generates an x-ray beam penetrating the radiography subject, and a radiation receiver which determines the radiation intensity behind the subject, a drive device for the measuring arrangement, a rotating frame for effecting rotational scanning movement of the measuring arrangement, and a measured value converter for the transformation of the signals delivered by the radiation receiver into a layer image, a stationary apparatus part and the rotating frame having a plurality of slip ring arrangements therebetween for the supply of current to the x-ray tube, each slip ring arrangement comprising two coaxial ring members (16, 21), of which one (16) is connected with the rotating frame (3), and the other is stationary, said coaxial ring members having sliding contacts (18, 19, 20) for the transmission of the x-ray tube current, said stationary part and rotating frame having interpenetrating axially projecting ribs (28 to 35), and having central openings (17, 22) of size to receive the patient support (1) therethrough, said plurality of slip ring arrangements having first and second slip rings (11, 13) in engagement with respective ones of the sliding contacts (18, 20) for conducting x-ray tube current during rotational scanning movement of the measuring arrangement, said interpenetrating axially projecting ribs defining first and second annular chambers (27, 36) containing the first and second slip rings (11, 13) respectively, and including oppositely axially projecting laterally overlapping annular ribs (29, 30, 33) of insulating material between said first and second annular chambers (27, 36) and defining a meandering air path between said first and second slip rings (11, 13), so as to electrically isolate said first and second slip rings with air without immersion thereof in insulating oil.

2. A tomographic x-ray apparatus according to claim 1, with the slip ring arrangement having said slip rings (11, 12, 13) on the coaxial ring member (16) connected with the rotating frame, the sliding contacts (18, 19, 20) being on the coaxial ring member (21) which is stationary.

3. A tomographic x-ray apparatus according to claim 1, with said slip ring arrangement having a total of three slip rings (11, 12, 13) for the purpose of supplying the high voltage and the filament voltage to the x-ray tube (4), two of the slip rings (11, 12) including said first slip ring and two of the sliding contacts (18, 19) cooperating therewith being connected to the cathode of the x-ray tube, said ribs (28 to 35) including sets of adjoining but axially offset ribs (28, 29, 33, 34) providing said first annular chamber (27) and said second annular chamber (36) between the coaxial ring members, the two slip rings (11, 12) and the two sliding contacts cooperating therewith being disposed in the first annular chamber (27), and said second slip ring (13) and a further one (20) of the sliding contacts cooperating therewith being disposed in the second annular chamber (36) and connecting with the anode of the x-ray tube.

* * * * *